United States Patent [19]
Muschler

[11] Patent Number: 5,824,084
[45] Date of Patent: Oct. 20, 1998

[54] METHOD OF PREPARING A COMPOSITE BONE GRAFT

[75] Inventor: George Frederick Muschler, Cleveland Heights, Ohio

[73] Assignee: The Cleveland Clinic Foundation, Cleveland, Ohio

[21] Appl. No.: 675,498

[22] Filed: Jul. 3, 1996

[51] Int. Cl.$^6$ .................................. A61F 2/28; A61F 2/02
[52] U.S. Cl. ............................................... 623/16; 623/11
[58] Field of Search .......................................... 623/16, 11

[56] References Cited

U.S. PATENT DOCUMENTS

| | | |
|---|---|---|
| 4,608,199 | 8/1986 | Caplan et al. . |
| 4,609,551 | 9/1986 | Caplan et al. . |
| 5,197,985 | 3/1993 | Caplan et al. . |
| 5,226,914 | 7/1993 | Caplan et al. . |
| 5,486,359 | 1/1996 | Caplan et al. . |

OTHER PUBLICATIONS

"The Origin of Bone Formed in Composite Grafts of Porous Calcium Phosphate Ceramic Loaded with Marrow Cells", by J. Goshima et al., Clinical Orthopoedics and Related Research, vol. 269, pp. 274–283, 1991.

*Primary Examiner*—John G. Weiss
*Assistant Examiner*—John M. Black
*Attorney, Agent, or Firm*—Calfee, Halter & Griswold LLP

[57] ABSTRACT

The present invention provides a new and improved method for preparing a composite bone graft. The method includes providing a bone marrow aspirate suspension and passing the bone marrow aspirate suspension through a porous, biocompatible, implantable substrate to provide a composite bone graft having an enriched population of connective tissue progenitor cells. Because the method is preferably performed intraoperatively it reduces the number of occasions the graftee must undergo invasive procedures. The invention also relates to an improved composite bone graft prepared according to the present method. The improved composite graft includes an enriched population of connective tissue progenitor cells and a greater number of connective tissue progenitor cells per unit volume than that found in the original bone marrow aspirate. The present invention also relates to a kit including the apparatus used for preparing the composite bone graft.

23 Claims, 5 Drawing Sheets

METHOD OF PREPARING A COMPOSITE BONE GRAFT

BACKGROUND OF THE INVENTION

Bone grafting is widely used to treat fractures, non-unions and to induce arthrodeses. Autogenous cancellous bone, which is taken from one site in the graftee and implanted in another site in the graftee, is currently the most effective bone graft. Autogenous cancellous bone provides the scaffolding to support the distribution of the bone healing response. Autogenous cancellous bone also provides the connective tissue progenitor cells which form new cartilage or bone. However, the harvest of autogenous bone results in significant cost and morbidity, including scars, blood loss, pain, prolonged operative and rehabilitation time and risk of infection. Furthermore, in some clinical settings, the volume of the graft site can exceed the volume of the available autograft. Accordingly, alternatives to autografts have been developed in an attempt to reduce the morbidity and cost of bone grafting procedures.

Several purified or synthetic materials, including ceramics, polymers, processed allograft bone and collagen-based matrices have been investigated or developed to serve as substitutes for autografts. The FDA has approved a porous coral derived synthetic hydroxyapatite ceramic for use in contained bone defects. A purified collagen/ceramic composite material is also approved for use in acute long bone fractures. Although these materials avoid the morbidity involved in harvesting autografts from the graftee and eliminate problems associated with a limited amount of available autograft, the clinical effectiveness of the synthetic materials remains generally inferior to autografts.

The synthetic graft materials have also been used as carriers for bone marrow cells. When such composite materials have been implanted into skeletal defects, the connective tissue progenitor cells differentiated into skeletal tissue. In some instances, the composite implants were made by soaking the synthetic graft material in a cell suspension obtained from a bone marrow plug. However, the connective tissue progenitor cells, which have the capacity to differentiate into cartilage, bone and other connective tissue such as fat, muscle, and fibrous tissue are present in the bone marrow in very minute amounts. The numbers of such cells present in 1 ml of bone marrow varies widely from subject to subject from about 100 cells to 20,000 cells. This represents a mean of about one in 20,000 to one in 40,000 of the nucleated cells in bone marrow. Thus, a composite implant made by soaking a given volume of synthetic carrier graft material in a comparable volume of fresh bone marrow contains relatively few connective tissue progenitor cells.

Accordingly, a technique has been previously developed to increase the relative concentration of connective tissue progenitor cells in composite implants. This technique involves plating a suspension of bone marrow cells onto tissue culture dishes, culturing the cells in a select medium for one or more days until the number of connective tissue progenitor cells in the culture increases, and then detaching the cells from the tissue culture dishes to provide a cell suspension containing a culturally-expanded population of connective tissue progenitor cells. Composite implants are then made by soaking synthetic ceramic carriers in this suspension of culturally-expanded cells. Unfortunately, this method of preparing composite implants is very time consuming. Moreover, if the culturally-expanded cells used in this method are derived from bone marrow aspirates obtained from the graftee, the graftee must undergo multiple invasive procedures, one to remove his or her bone marrow and one at a later date to implant the composite implant. In addition, the graftee may be exposed to anaesthesia more than once.

Accordingly it is desirable to have a new method of preparing a composite bone marrow graft which can be performed intraoperatively, i.e., at the same time bone marrow is being taken from the graftee. An intraoperative method of preparing a composite bone marrow graft which uses bone marrow aspirate as the source of the connective tissue progenitor cells and which results in the formation of a composite bone graft containing an enriched population of connective tissue progenitor cells is especially desirable.

SUMMARY OF THE INVENTION

The present invention provides a new and improved method for preparing a composite bone graft. As used hereinafter the term "bone graft" refers to a graft which comprises connective tissue progenitor cells and is, therefore, capable of differentiating into cartilage or bone. The method comprises providing a bone marrow aspirate suspension and passing the bone marrow aspirate suspension through a porous, biocompatible, implantable substrate to provide a composite bone graft having an enriched population of connective tissue progenitor cells. Because the method is preferably performed intraoperatively using a bone marrow aspirate from the graftee, it reduces the time and expense required for graft preparation and also the number of times the graftee must return to the operating room to undergo invasive procedures. The improved composite bone graft prepared by the present method contains an enriched population of connective tissue progenitor cells and a greater number of connective tissue progenitor cells per unit volume than that found in the original bone marrow aspirate.

The present invention also relates to the composite bone marrow graft prepared according to the present method and a kit comprising the apparatus for preparing the composite bone graft.

DETAILED DESCRIPTION OF THE INVENTION

Figure 1:
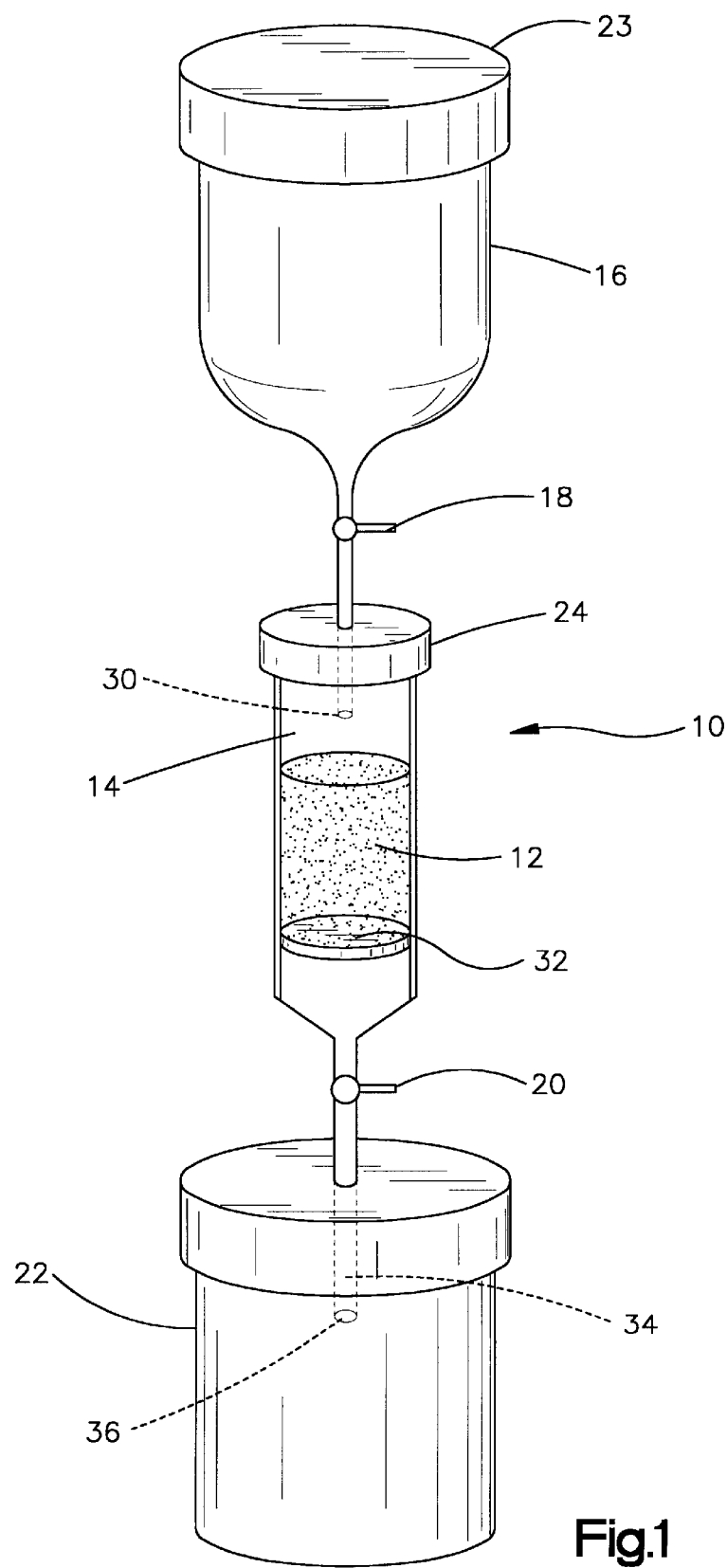
FIG. 1 is a representation, somewhat schematic, of an apparatus used to prepare a composite bone graft in accordance with the present invention.

The present invention provides a new and improved method for preparing a composite bone graft. The method comprises collecting a bone marrow aspirate from a donor, preferably in the presence of an anti-coagulant to provide a bone marrow aspirate suspension, and passing the bone marrow aspirate suspension through a porous, biocompatible, implantable substrate. Preferably, the method is performed intraoperatively using a bone marrow aspirate preferably from the graftee.

Preparing A Bone Marrow Aspirate Suspension

Bone marrow aspirate contains plasma, nucleated connective tissue progenitor cells, other nucleated cells of hematopoietic origin, nucleated endothelial cells, and cells derived from contaminating peripheral blood. Since bone marrow aspirate also contains peripheral blood, it is preferred that the bone marrow be collected in a syringe containing an anti-coagulant. Suitable anti-coagulants include, for example, heparin, sodium citrate, EDTA and dextran. Preferably, the bone marrow aspirate is mixed with a sterile isotonic solution to provide a concentration in the range of from about 10 million to about 300 million nucleated cells/ml, preferably from about 20 million to about 250 million nucleated cells/ml, more preferably from about 50 million to about 200 million nucleated cells/ml. Suitable isotonic solutions include, for example, isotonic buffered salt solutions, such as Hank's Balanced Salt Solution and phosphate buffered saline, and tissue culture medium such as minimal essential medium. As used herein, the term "bone marrow aspirate suspension" refers to a bone marrow aspirate that has not been mixed with an isotonic solution and to a bone marrow aspirate that has been mixed with an isotonic solution.

Substrate

The substrate is made from a biocompatible, implantable graft material. Preferably, the material has a charged surface. Examples of biocompatible, implantable graft materials having a charged surface include synthetic ceramics comprising calcium phosphate, some polymers, demineralized bone matrix, or mineralized bone matrix.

More preferably, cell adhesion molecules are bound to the surface of the substrate. The term "cell adhesion molecules" refers collectively to laminins, fibronectin, vitronectin, vascular cell adhesion molecules (V-CAM) and intercellular adhesion molecules (I-CAM) and collagen.

Preferably, the substrate has a sufficient number of pores or passageways so that the total surface area of the substrate is at least five times greater than a solid object having the same external dimensions. Thus, the preferred total surface area can be achieved by using a substrate which comprises a mass of powder, a mass of granules, a mass of fibers, or a highly porous block of substrate material. Preferably, the size of the pores in the substrate is greater that 20 $\mu$, more preferably greater than 40 $\mu$, most preferably greater than 100 $\mu$.

Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, and granular ceramics such as that incorporated into the bone graft substitute Collagraft sold by Zimmer, or filamentous sponges such as those made from collagen by Orquest.

Substrate Container

Preferably, the substrate is disposed in a container configured to retain the substrate in the container and to allow fluid and bone marrow cells to flow through the container. This is accomplished by using a container having two openings at either end thereof and comprising a member having one or more pores disposed between the substrate and one of the openings. Preferably, the pores of the member have a diameter of sufficient size to allow fluid and cells to flow therethrough and to retain the substrate in the container. Preferably, the length of the container is greater than the width of the container to increase residence time of the suspension in the substrate.

Preferably, the container is made of a material which is biocompatible and pyrogen-free. Suitable container materials include for example glass, plastic or metal. Although the container may comprise two fluid flow restrictors blocking the openings at either end of the container, preferably, a fluid flow regulator is attached to at least one end of the container to regulate flow of the bone marrow aspirate suspension through the substrate.

Conditions

Preferably, the bone marrow aspirate suspension is permitted to flow through the substrate under hydrostatic pressure which may be generated by external forces or the force of gravity. Preferably, the linear elution rate of the suspension through the substrate is between 2 and 500 mm/minute, more preferably between 5 and 200 mm/minute, most preferably between 10 and 100 mm/minute.

Optionally, the effluent is collected sterilely in an effluent collector and recycled through the substrate one or more times to increase the number of connective tissue progenitor cells in the composite bone graft.

Optionally, a wash solution is passed through the substrate after the original bone marrow aspirate suspension and any effluents have been passed through the substrate. Preferably, the wash solution comprises a sterile, isotonic, buffered solution having a pH range of 7.3 to 7.5. Suitable wash solutions include, for example, phosphate-buffered saline, Hank's balanced salt solution, and minimal essential medium.

Optionally, growth factors or additional cells which secrete growth factors are added to the composite bone graft prior to use. Growth factors which may be added include for example, fibroblast growth factor, epithelial growth factor, transforming growth factor Beta, insulin-like growth factor, and bone morphogenic protein. Preferably, growth factors are added by passing a solution containing the growth factors through the substrate after all previous suspensions and solutions have been passed through the substrate. Alternatively, grow factors are added by incorporation into the wash solution.

The following examples of methods of preparing a composite bone graft are intended to illustrate but not to limit the present invention:

EXAMPLE 1

The present method for preparing a composite bone graft may be more readily understood by reference to FIG. 1 which depicts a preferred embodiment of the apparatus for performing the method. The apparatus, shown generally as 10, comprises a porous, biocompatible, implantable substrate 12, a container 14, for holding substrate 12, a reservoir 16 for holding the bone marrow aspirate suspension, a first fluid flow regulator 18, a second fluid flow regulator 20, and an effluent collector 22. Prior to preparation of the composite bone graft, all of the components of the apparatus are sterilized. Following removal of top 23, the bone marrow aspirate suspension is introduced into reservoir 16. Then fluid flow regulator 18 is opened to allow the bone marrow aspirate suspension to flow out of reservoir 16 and into opening 30 in removable top 24 of container 14 and onto substrate 12.

As the suspension enters substrate 12, fluid flow regulator 20 which is attached to tip 34 of container 14 is opened to permit the effluent of the bone marrow aspirate suspension to flow through porous member 32, through opening 36 of container 14 and into effluent collector 22.

Reservoir 16 and removable top 24 are then detached from container 14 and the improved composite bone marrow graft is then removed from container 14. The improved composite bone graft, which comprises substrate 12, an enriched population of connective progenitor cells and a heterogenous population of other nucleated bone marrow cells is ready to use as an implant or in vitro.

EXAMPLE 2

Nine cylindrical disks of coralline hydroxyapatite (HA) measuring 13 mm in diameter and 5 mm in thickness were obtained from Interpore, Inc., Irvine, Calif. Each disk was placed in the tip of a vertically mounted 10 cc syringe barrel fitted with a stopcock. Marrow samples were taken from the anterior iliac crest of nine volunteer human subjects by aspiration. Samples were collected using a Lee-Lok bone marrow aspiration needle and a 10 cc syringe containing 1 ml of normal saline and 1000 units of Sodium-Heparin. Two ml of bone marrow were aspirated from each site. Marrow samples were suspended in α-MEM to prepare a suspension of marrow cells containing 50 million nucleated cells per ml. 2 ml of the marrow cell suspension were introduced in to the top of the syringe and the stopcock was adjusted to allow the marrow cell suspension to elute through the disk at 2 ml/minute. Each sample of effluent was recycled through the disk three times. After the effluent was collected, the disk was washed with 6 ml phosphate buffered saline at an elution rate of 2 ml/min, to remove loosely adherent cells and to produce the composite bone graft.

The number of nucleated cells in the initial suspension, the effluents, and the washes were counted using a hemocytometer to determine the number of nucleated cells retained in the resulting composite bone grafts. To determine the number of connective tissue progenitors retained in the resulting composite bone grafts, the number of connective tissue progenitors in the initial suspensions, the effluent, and the washes were assayed by colony counting on tissue culture plastic. For colony counting, 500,000 nucleated cells from the original suspension, the effluents and the wash were plated in separate 35 mm diameter tissue culture wells and cultured in α-MEM containing dexamethasone ($10^{-8}$M) and ascorbate (50 mg/ml) for 9 days. The cultured cells were then stained for alkaline phosphatase activity using a N', N', dimethyl naphthol M-X phosphate as a substrate and Texas Fast Red as a counter-stain. Alkaline phosphatase activity is a marker of osteoblastic differentiation. Thus, the number of colonies which stain positively for alkaline phosphatase activity reflect the number of connective tissue progenitors present in the original suspension, the effluents and the wash.

The number of nucleated cells and connective tissue progenitor cells which were retained on the substrate following each step were calculated by subtracting the number of nucleated cells and connective progenitor cells found in the effluents or wash from the number of nucleated cells and connective tissue progenitor cells in the initial suspension. The average number of nucleated cells and connective tissue progenitor cells retained in the nine composite bone grafts and the percentage of nucleated cells and connective tissue progenitor cells retained in the composite bone grafts are shown in Table 1.

EXAMPLE 2

Composite bone grafts were prepared as described in Example 1 except that bone marrow samples were taken from the anterior iliac crest of three different volunteer human subjects and the substrates used were cylindrical disks of demineralized human cancellous bone matrix obtained from Life Net, Virginia Beach, Va.

The number of nucleated cells and connective tissue progenitor cells retained in the composite grafts were determined as described above in example 1. The average number of nucleated cells and connective tissue progenitor cells retained in the composite bone grafts and the percentage of nucleated cells and connective tissue progenitor cells retained in the composite bone grafts are shown in Table 1.

TABLE 1

Retention of Cells in Composite Bone Grafts made using disks of hydroxyapatite or demineralized human cancellous bone

|  | HA Disks | Cancellous Bone |
|---|---|---|
| Nucleated Cells in Original Suspension | $100 \times 10^6$ | $100 \times 10^6$ |
| Nucleated Cells Retained before Wash | $56.45 \times 10^6$ | $40.00 \times 10^6$ |
| Nucleated Cells Removed with Wash | $9.12 \times 10^6$ | $15.78 \times 10^6$ |
| Nucleated Cells Retained after Wash | $47.33 \times 10^6$ | $24.22 \times 10^6$ |
| CTPC in Original Suspension | 7800 | 11100 |
| CTPC Retained After Wash | 5162 | 4950 |
| Percent of all Nucleated Cells Retained | 47% | 24% |
| Percent of all CTPC Retained | 66% | 44% |
| Ratio of CTPC to Nucleated cells | 1.4 | 1.8 |
| Concentration of CTPC in Composite Bone Graft vs Concentration of CTPC in Original Suspension | 2.8 | 1.3 |

CTPC = Connective Tissue Progenitor Cells

As shown in Table 1, composite grafts made with a substrate of hydroxyapatite or demineralized human cancellous bone retained a significant percentage of the nucleated cells (47% and 24%, respectively) and an even greater percentage of the connective tissue progenitor cells (66% and 44%, respectively) in the original suspension. As also shown in Table 1, washing substrates of cancellous bone or coralline hydroxyapatite resulted in removal of a mean of 16.2% (range 10%–33%) of the nucleated cells which are initially retained in a coralline HA substrates and 39.45% (range 33–86%) of the cells retained in a demineralized cancellous bone matrix substrates.

As shown in table 1, the composite grafts made with either the hydroxyapatite or the demineralized human cancellous bones selectively retained the connective tissue progenitor cells as compared to other marrow derived nucleated cells. This selective retention is illustrated by the ratio (>1) of % connective tissue progenitor cells retained vs % nucleated cells retained on the substrate. Thus, the composite bone grafts prepared with either the hydroxyapatite disks or the demineralized human cancellous bone disks comprise an enriched population of connective progenitor cells.

Concentration of connective tissue progenitor cells above that found in the original bone marrow sample is illustrated by dividing the number of connective tissue progenitor cells retained by the volume of the disks (0.63 cm$^3$). As shown in Table 1, the mean concentration of connective tissue progenitor cells retained in the composite bone grafts comprising HA disks was 2.8 times greater than the concentration in the original marrow sample. Similarly, the mean concentration of connective tissue progenitor cells retained in the composite bone grafts comprising demineralized cancellous bone matrix was 1.3 times greater than in the original marrow sample.

EXAMPLE 3

Forty-five composite bone grafts were prepared as described in Example 1 except that the concentration of nucleated cells in the marrow suspension was varied between 5, 10, 20, 40, and 50 million cells/ml from each of the nine human donors. The number of nucleated cells and connective tissue progenitor cells retained on cells retained on each of the resulting composite bone grafts were determined as described in Example 1. The results are shown in FIGS. 2a and 2b.

Figure 2A:
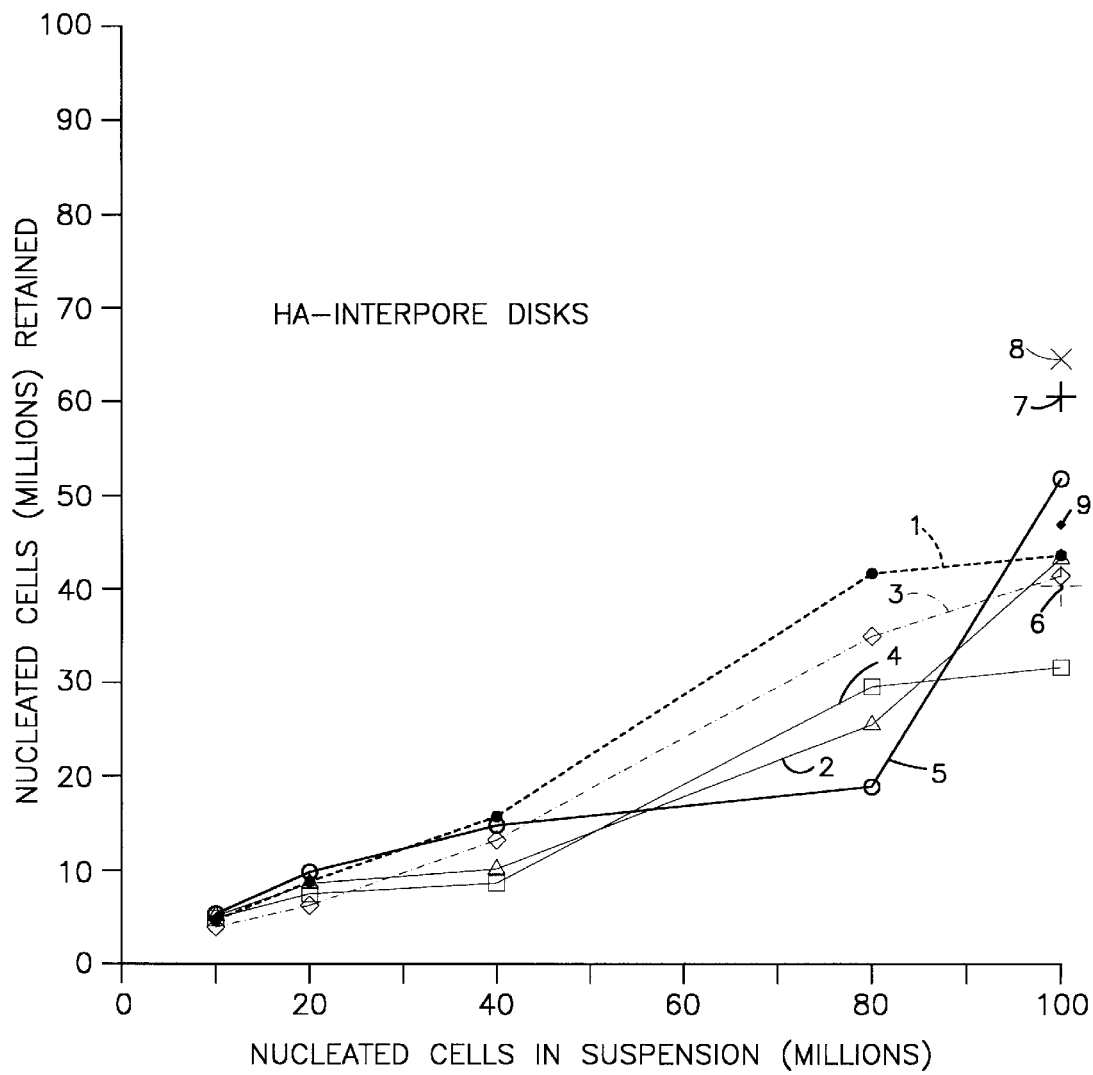
FIG. 2a is a graph showing the effect of increasing the concentration of nucleated cells in the bone marrow aspirate suspension on the number of nucleated cells retained on a composite bone graft comprising a hydroxyapatite substrate.
Figure 2B:
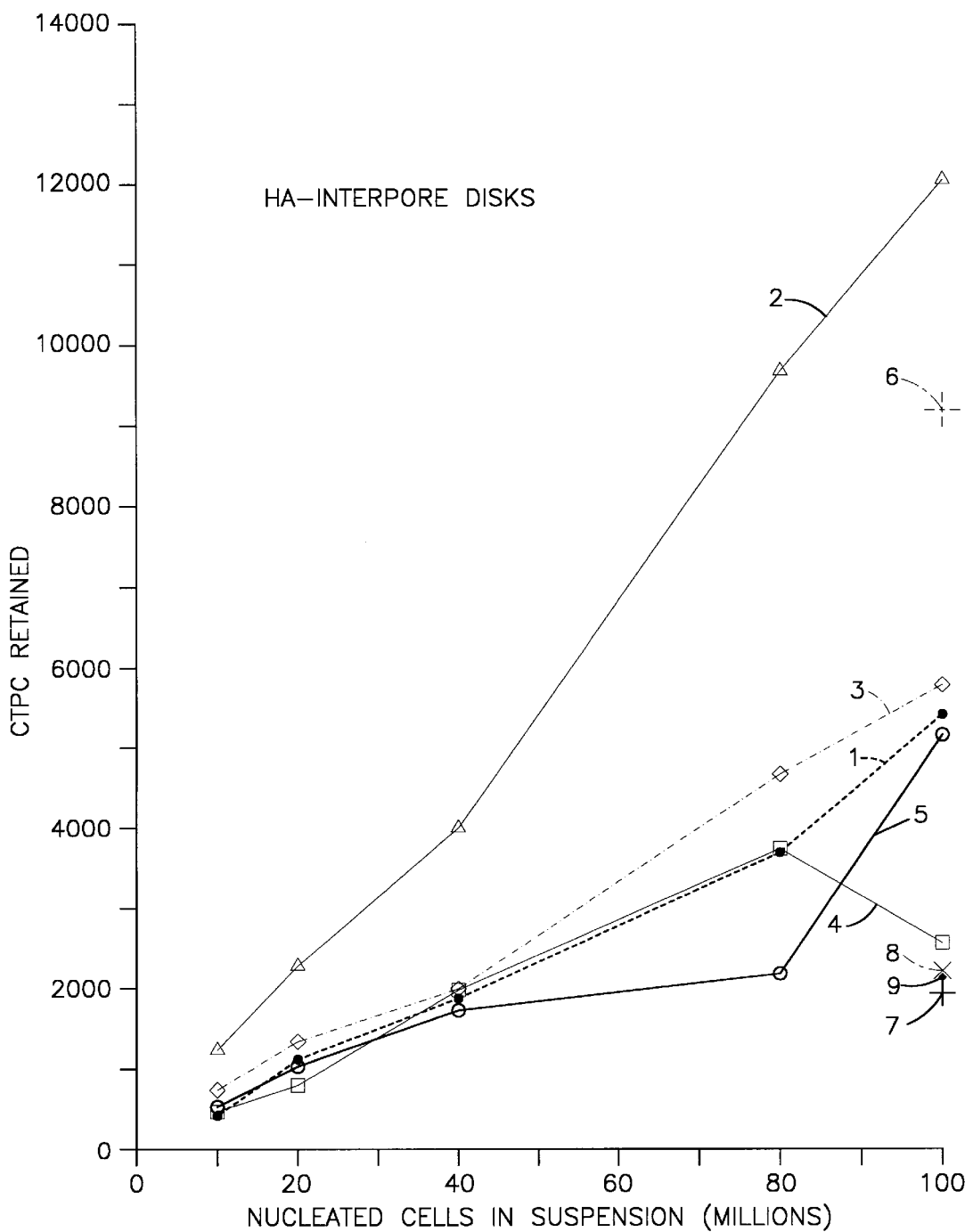
FIG. 2b is a graph showing the effect of increasing the concentration of nucleated cells in the bone marrow aspirate suspension on the number of connective tissue progenitor cells retained on a composite bone graft comprising a hydroxyapatite substrate.

As shown in FIGS. 2a and b, the number of nucleated cells and the number of connective tissue progenitor cells retained in the composite bone grafts increased in an essentially linear fashion as the number of marrow cells passed through the hydroxyapatite substrate was increased, indicating that saturation of the hydroxyapatite substrate with marrow derived cells did not occur over the range of cells to substrate volume evaluated.

EXAMPLE 4

Fifteen composite bone grafts were prepared using disks of demineralized cancellous bone matrix as described in Example 2 except that the concentration of nucleated cells in the marrow suspension was varied between 5, 10, 20, 40, and 50 million cells/ml from each of the three human donors. Data reflecting the number of nucleated cells and the number of connective tissue progenitor colonies retained in the resulting composite bone grafts is presented in FIGS. 3a and 3b.

Figure 3A:
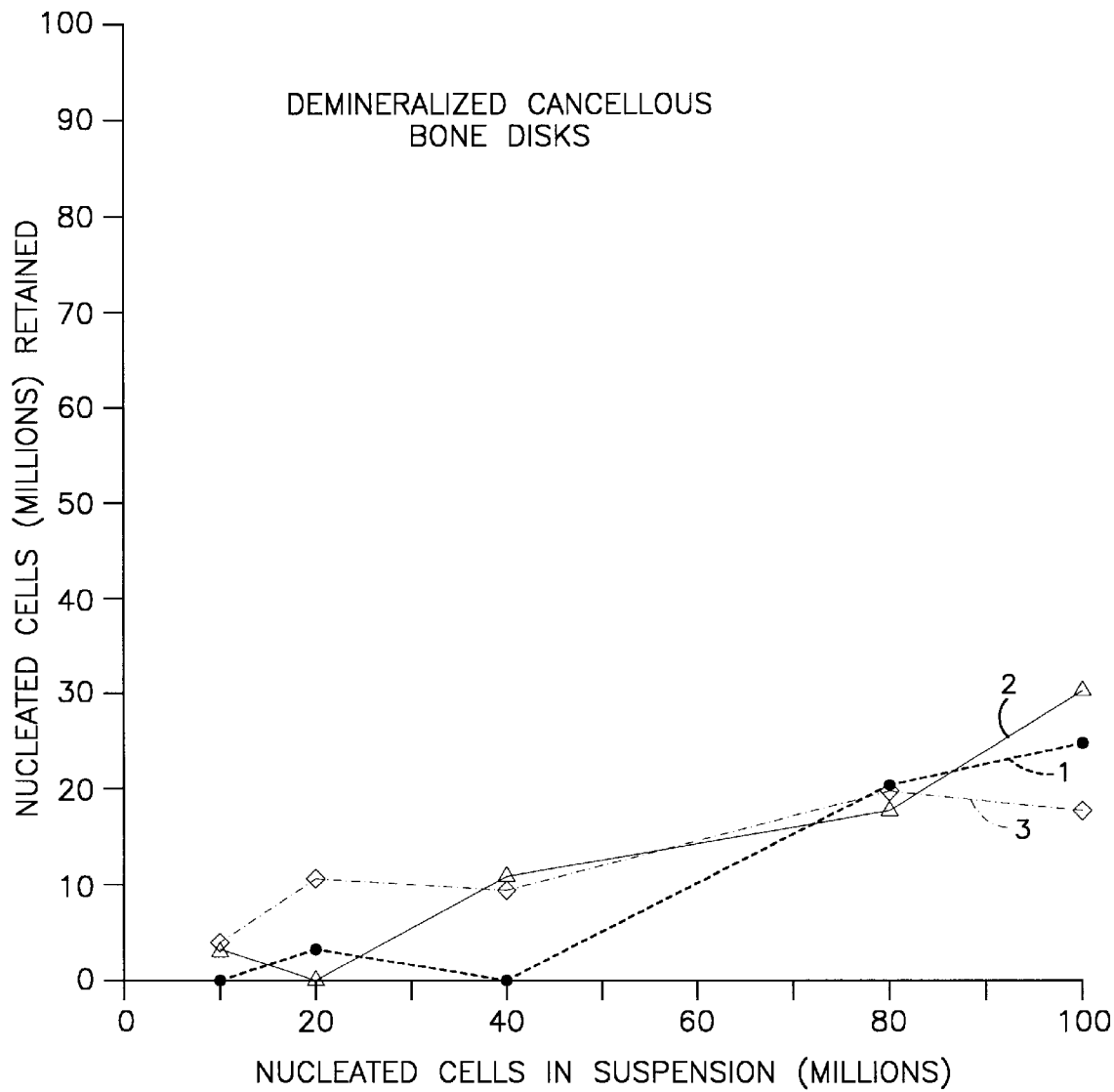
FIG. 3a is a graph showing the effect of increasing the concentration of nucleated cells in the bone marrow aspirate suspension on the concentration of nucleated cells retained on a composite bone graft comprising a demineralized human cancellous bone matrix substrate.
Figure 3B:
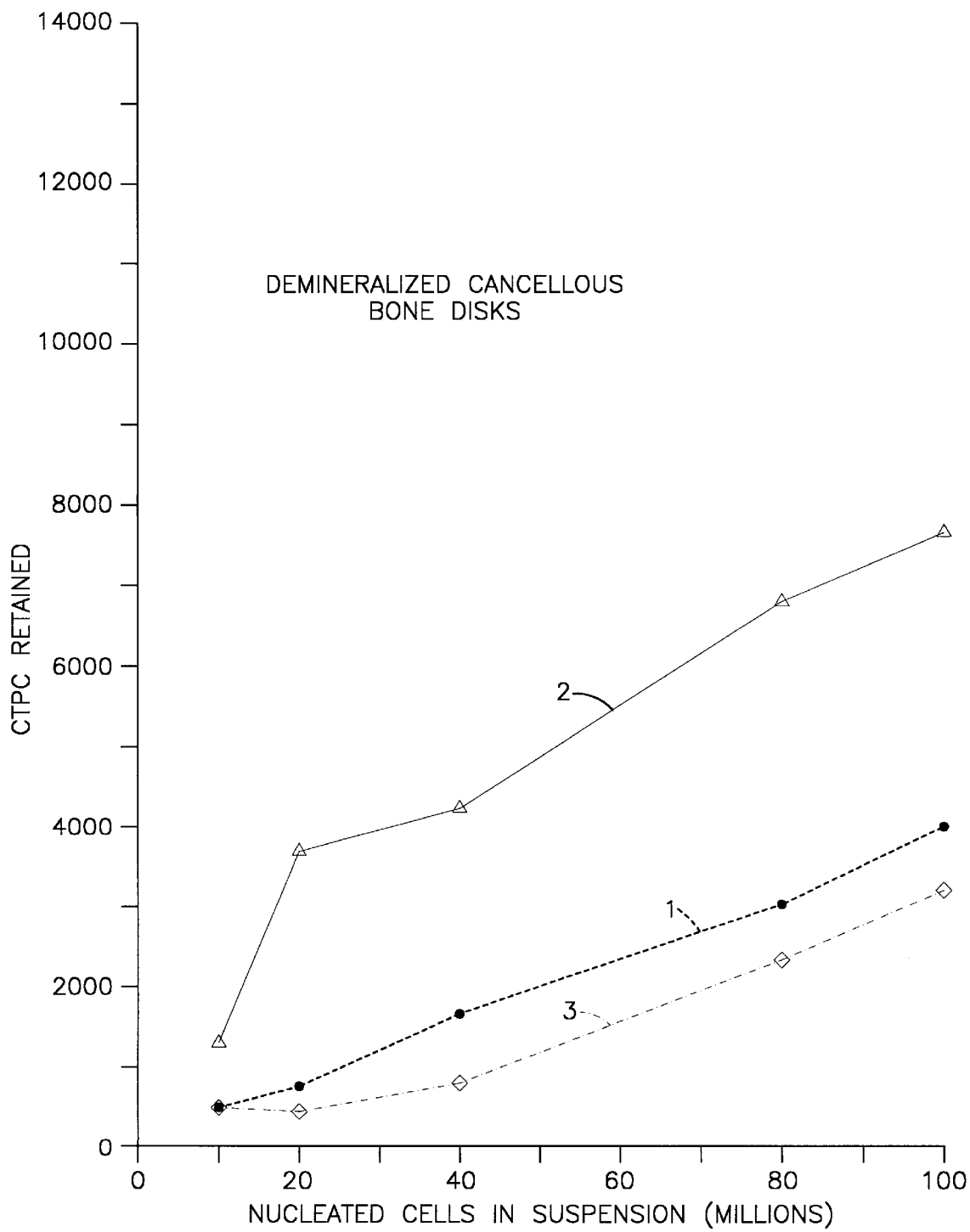
FIG. 3b is a graph showing the effect of increasing the concentration of nucleated cells in the bone marrow aspirate suspension on the number of connective progenitor cells retained on a composite bone graft comprising a demineralized human cancellous bone matrix substrate.

As shown in FIGS. 3a and 3b, the number of nucleated cells and the number of connective tissue progenitor cells retained in the composite bone grafts increased in an essentially linear fashion as the number of marrow cells passed through the demineralized cancellous bone matrix substrate increased, indicating that saturation of the substrate with marrow derived cells did not occur over the range cells to substrate volume evaluated.

EXAMPLE 5

A composite bone graft was prepared as described in Example 1 using a 2 cc marrow suspension containing 5 million nucleated cells/ml except that the substrate was not washed with 6 ml of phosphate buffered saline after loading. Compared to an identical disk loaded in an identical manner which was washed as in example 1, the unwashed disk retained the same number of connective tissue progenitors (1000 in the case shown) and a greater number of marrow derived nucleated cells (2.2 million vs 1.2 million in the washed example). After culture for 24 days in vitro, the presence of these additional cells resulted in greater proliferation and differentiation of the connective tissue progenitors. This was manifest by a greater surface area covered by cells that expressed alkaline phosphatase activity, which is a marker of osteoblastic differentiation.

EXAMPLE 6

A composite bone graft was prepared as in example 1 except that the bone marrow suspension was recycled over the hydroxyapatite disk only once, rather than three times. This reduced the number of cells and connective tissue progenitors which remained attached to the disk of coralline hydroxyapatite.

EXAMPLE 7

Three composite bone grafts were prepared as in example 1 except that the concentration of nucleated cells in the marrow suspension was increased from 100 to 150 million nucleated cells per ml. This increase in the number of cells passed through the hydroxyapatite disks increased the number of nucleated cells and connective tissue progenitor cells retained in the composite bone grafts by a mean of 66.84% and 52.0%, respectively. These highly cellular suspensions exhibited increased viscosity and slower elution flow rates.

These methods of preparing composite bone marrow grafts typically required less than sixty minutes to complete. Thus, these methods can be performed while the bone marrow donor/graftee is in the operating room. Accordingly, the number of occasions the graftee must undergo invasive procedures to receive a composite bone graft can be reduced by using these methods.

The improved composite bone grafts prepared according to these methods comprised a biocompatible, implantable substrate and an enriched population of connective tissue progenitor cells. As used herein the term "enriched population of connective tissue progenitor cells" means that the percentage of connective tissue progenitor cells as compared to all nucleated bone marrow cells is greater in the composite bone marrow graft than in the original bone marrow aspirate. In addition, the concentration of the connective tissue progenitor cells in the improved composite bone marrow grafts was about two times greater than the concentration of these cells in the original aspirate.

The improved composite bone grafts also comprised a population of nucleated cells other than connective tissue progenitor cells, including endothelial cells and hematopoietic cells derived from bone marrow, and a population of platelets derived from peripheral blood. The red blood cells and plasma in the bone marrow aspirate suspension are not selectively retained in the composite bone grafts and, thus, the improved composite bone grafts typically contain less than five % of the red blood cells in the original suspension.

The improved composite bone graft is suitable for implantation into the bone marrow aspirate donor or into an immunologically compatible host. The improved composite bone graft is also useful for assessing the effect of cytokines, hormones and other biochemical molecules on the proliferation and differentiation of connective tissue progenitor cells in vitro.

The present invention also provides a method for increasing the concentration of connective tissue progenitor cells in an isolated population of bone marrow cells. The method comprises passing a bone marrow aspirate suspension through a porous biocompatible, implantable graft material to provide a matrix with nucleated bone marrow cells chemically bonded thereto, disassociating the nucleated bone marrow cells from the matrix with a solution capable of disrupting the chemical bonds between the matrix and the nucleated bone marrow cells, and then collecting the disassociated cells. Suitable solutions for disassociating the nucleated bone marrow cells from the matrix include for example, medium containing trypsin, growth medium containing a chelator such as for example EGTA. To further increase the relative concentration of connective tissue progenitor cells in the isolated population of nucleated bone marrow cells, a wash solution is passed through the matrix before the cells are disassociated therefrom.

What is claimed is:

1. A method for preparing an improved composite bone graft comprising the steps of:

(a) providing a bone marrow aspirate suspension; and (b) passing the bone marrow aspirate suspension through a porous, biocompatible, implantable substrate to provide an effluent and a composite bone graft, said composite bone graft comprising said substrate and a heterogeneous population of nucleated bone marrow cells and an enriched population of connective tissue progenitor cells.

2. The method of claim 1 wherein said bone marrow aspirate suspension comprises an anti-coagulant.

3. The method of claim 2 further comprising the step of recycling the effluent of the bone marrow aspirate suspension through said substrate.

4. The method of claim 2 further comprising the step of washing said substrate after the bone marrow aspirate suspension has been passed through said substrate.

5. The method of claim 3 further comprising the step of washing said substrate after the effluent has been recycled through said substrate.

6. The method of claim 1 wherein said substrate comprises a graft material selected from the group consisting of a synthetic ceramic comprising calcium phosphate, mineralized bone, demineralized bone, and collagen.

7. The method of claim 1 wherein said substrate has external dimensions and a total accessible surface area at least five times greater than a solid object having the same external dimensions.

8. The method of claim 1 further comprising the step of passing a solution comprising growth factors through said substrate.

9. The method of claim 7 wherein said substrate comprises cell adhesion molecules bonded to the surface thereof.

10. The method of claim 1 wherein an isotonic solution is added to said bone marrow aspirate before step (a) to provide a bone marrow aspirate suspension having a concentration range of from about 10 million nucleated cells/ml to about 300 million nucleated cells/ml.

11. The method of claim 1 wherein said bone marrow aspirate suspension has a linear elution rate through said substrate of from about 2 mm/minute to about 500 mm/minute.

12. The method of claim 1 wherein said substrate is disposed in a container configured to retain the substrate in the container and to allow fluid and cells to flow through the container.

13. The method of claim 10 wherein the bone marrow aspirate suspension has a concentration range of from about 20 million nucleated cells/ml to about 250 million nucleated cells/ml.

14. The method of claim 1 further comprising the step of recycling the effluent through said substrate.

15. The method of claim 1 further comprising the step of washing said substrate after the bone marrow aspirate suspension has been passed through said substrate.

16. The method of claim 2 wherein said substrate comprises a graft material selected from the group consisting of a synthetic ceramic comprising calcium phosphate, mineralized bone, demineralized bone, and collagen.

17. The method of claim 2 wherein said substrate has external dimensions and a total accessible surface area at least five times greater than a solid object having the same external dimensions.

18. The method of claim 2 further comprising the step of adding growth factors to the composite bone graft.

19. The method of claim 2 wherein cell adhesion molecules are bound to the surface of the substrate.

20. The method of claim 2 wherein an isotonic solution is added to said bone marrow aspirate before step (a) to provide a bone marrow aspirate suspension having a concentration range of from about 10 million nucleated cells/ml to about 300 million nucleated cells/ml.

21. The method of claim 2 wherein said bone marrow aspirate suspension has a linear elution rate through said substrate of from about 2 mm/minute to about 500 mm/minute.

22. (New) The method of claim 2 wherein said substrate is disposed in a container configured to retain the substrate in the container and to allow fluid and bone marrow cells to flow through the container.

23. The method of claim 20 wherein the bone marrow aspirate suspension has a concentration range of from about 20 million nucleated cells/ml to about 250 million nucleated cells/ml.

* * * * *